United States Patent [19]

Huffman

[11] 4,036,873

[45] July 19, 1977

[54] PREPARATION OF ALKYL SUBSTITUTED o-HYDROXYBENZOIC ACID ESTERS

[75] Inventor: Clarence W. Huffman, Clark, N.J.

[73] Assignee: IMC Chemical Group, Inc., Newark, N.J.

[21] Appl. No.: 556,476

[22] Filed: Mar. 7, 1975

[51] Int. Cl.$^2$ .............................................. C07G 69/76
[52] U.S. Cl. .............................. 260/473 S; 260/520 A
[58] Field of Search ......................... 260/473 S, 520 A

[56] References Cited

PUBLICATIONS

March, Jerry, "Advanced Organic Chemistry:Reactions, Mechanisms, and Structure," McGraw-Hill Book Co., N. Y. (1967) pp. 420–421.

Primary Examiner—Paul J. Killos
Attorney, Agent, or Firm—Pennie & Edmonds

[57] ABSTRACT

A process for producing $C_1$-$C_5$ alkyl substituted o-hydroxybenzoic acid esters comprising forming an anhydrous alkali metal phenolate-organic carrier mixture, carboxylating the phenolate by contacting the mixture with $CO_2$ and reacting the resultant dialkali metal salt with 1 equivalent of an anhydrous acid/mole of salt and at least 1 mole of $C_1$-$C_5$ alkyl chloride per mole of salt.

21 Claims, No Drawings

PREPARATION OF ALKYL SUBSTITUTED o-HYDROXYBENZOIC ACID ESTERS

BACKGROUND OF THE INVENTION

The Kolbe and Kolbe-Schmitt reactions have long been a standard procedure for the preparation of aromatic hydroxy acids, such as salicylic acid and its derivatives. The procedures require the initial formation of a dry powdered metal phenolate which is then carboxylated with carbon dioxide at elevated temperature and pressure. If the ester is desired, it is normally formed by reaction with the appropriate alcohol. Due to the pressure requirements needed for the carboxylation, special autoclave reactors are required which have provisions for continuous stirring and grinding of the solid phenolate. The requirement to initially form a dry powdered phenolate before carrying out the carboxylation as well as the need for special autoclave equipment has mitigated against the widespread use of the Kolbe process or the Schmitt modification thereof. It has long been desired to simplify the process in a manner which would eliminate the need to first form a dry material and also the need for special equipment.

SUMMARY OF THE INVENTION

It has now been found possible to prepare alkyl esters of o-hydroxybenzoic acids without the need for high pressures during carboxylation, without the need to initially form a dry phenolate, and without the need for separately esterifying the formed acid, by a direct alkylation of the formed salt. The present process allows for the elimination of separating and handling the intermediate products formed during the process.

The present invention comprises a process of producing an alkyl ester of o-hydroxybenzoic acids, comprising reacting an alkyl substituted phenol with an alkali metal hydroxide, dehydrating to form a substantially anhydrous alkali metal phenolate-organic carrier mixture, carboxylating the phenolate by contacting the mixture with $CO_2$ at an elevated temperature to form a dialkali metal salt, acidifying with about one mole of acid per mole of salt and reacting with at least one mole of alkyl chloride per mole of salt.

DETAILED DESCRIPTION OF THE INVENTION

The instant invention is a new and novel process for the preparation of alkyl substituted o-hydroxybenzoic acid esters of the general formula:

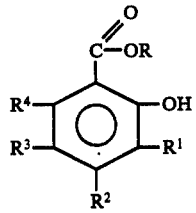

wherein R is a $C_1$-$C_3$ alkyl, $R^1$, $R^2$, $R^3$ and $R^4$ are each selected from hydrogen or a $C_1$-$C_3$ alkyl provided that at least one of $R^1$, $R^2$, $R^3$ or $R^4$ is a $C_1$-$C_3$ alkyl comprising reacting an alkali metal hydroxide with an alkyl substituted phenol of the general formula:

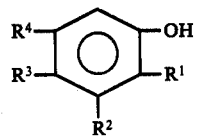

wherein $R^1$, $R^2$, $R^3$ and $R^4$ have the same meaning as above to form an essentially anhydrous alkali metal phenolate-organic carrier mixture; carboxylating the phenolate by contacting said mixture with sufficient carbon dioxide to form a dialkali metal salt of the general formula

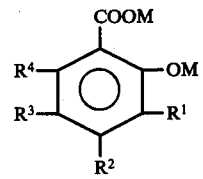

wherein M represents the alkali metal and $R^1$, $R^2$, $R^3$ and $R^4$ are the same as above; acidifying the salt, while still in the organic carrier, with about 1 mole of acid per mole of salt; and reacting the salt with at least about one mole of a $C_1$-$C_5$ alkyl chloride per mole of salt. The alkyl substituted o-hydroxybenzoic acid esters are easily separated from the product-organic carrier mixture by fractional distillation.

The alkyl substituted o-hydroxybenzoic acid esters of this invention are useful industrial solvents. Methyl cresotinate, as an example, is extensively used as a solvent dye carrier in the textile industry.

The alkali metal phenolate is formed by reacting an alkali metal hydroxide with an alkyl substituted phenol corresponding to the finished product desired. For example, o-cresol is used to form o-cresotinic acid esters. Any alkali metal hydroxide can be used with sodium hydroxide and potassium hydroxide being preferred because they are readily available. Some alkali metal phenolates tend to allow the carboxylation to occur at both the ortho and para positions with respect to the hydroxy group. When $R^3$ is $C_1$-$C_3$ alkyl substituted or when the phenolate is formed with sodium hydroxide the carboxylation is substantially directed ortho. Sodium hydroxide is the preferred alkali metal hydroxide.

The phenolate formation can be performed in an aqueous media or in an aqueous-organic media. When the phenolate is formed in an aqueous media the aqueous-phenolate mixture is added to an amount of organic carrier in excess of the amount needed to assist in the removal of the $H_2O$ present. The water is removed by heating under atmospheric or reduced atmospheric pressure to form a substantially anhydrous alkali metal phenolate-organic carrier mixture. Alternately, the organic carrier can be present during the formation of phenolate. The water present can thus be removed simultaneously with its introduction into the mixture (as by-product in phenolate formation and from aqueous alkali metal hydroxide) to yield a substantially anhydrous alkali metal phenolate-organic carrier mixture.

The organic carrier can be a non-polar organic liquid which is substantially insoluble in water. Examples are cumene, xylene, toluene, benzene and the like. The non-polar organic liquid can obtain up to 50 percent of a $C_7$-$C_{14}$ alcohol which is also substantially insoluble in water. Examples are 1-hexanol, 2-hexanol, 3-hexanol, 2-ethyl-1-hexanol, 2-methyl-1-hexanol, 2-methyl-2-hexanol, 1-heptanol, 2-heptanol, 4-methyl-4-heptanol, 1- decanol, 1-dodecanol and the like. The organic carrier should have a boiling point higher than about 130° C. in order to perform the carboxylation at atmospheric pressure or slightly above as discussed below. The use of carriers having a lower boiling point, such as toluene or benzene requires the utilization equipment capable of maintaining moderate pressure during carboxylation.

It has been found that carboxylation of the alkali metal phenolate can be performed by contacting the phenolate-organic carrier mixture with sufficient carbon dioxide to form the dialkali metal salt of formula III above. Although one mole of carbon dioxide is needed for every two moles of phenolate, normally an excess of carbon dioxide is used to ensure completion. The carbon dioxide can be contacted with the mixture in any manner, such as by bubbling of carbon dioxide gas through the mixture. The carboxylation is run at elevated temperatures of about 100° to about 150° C. and preferably between about 130° to 150° C. By utilizing high boiling organic carriers, such as xylene or xylene:2-ethyl-1-hexanol mixture, the carboxylation can be run at substantially atmospheric pressure or slightly above to prevent loss of solvent vapors into the atmosphere.

As stated above the carboxylation occurs substantially totally in the ortho position when using sodium phenolate or an alkali phenolate in which $R^3$ is alkyl substituted.

The dialkali metal salt-organic carrier mixture obtained from the carboxylation, without further purification or separation, can be transformed into the desired alkyl substituted o-hydroxybenzoic acid ester in accordance with the present process. The dialkali metal salt is acidified with about 1 equivalent of an inorganic acid per mole of salt. The acid should be in a substantially anhydrous state. Although any anhydrous inorganic acid can be used, hydrochloric, hydrobromic, phosphoric and sulfuric acids are preferred. Commercial dry HCl is the most preferred acid. The salt is also reacted with an alkyl chloride to form the appropriate ester. The alkyl chloride can be any $C_1$-$C_5$ alkyl chloride such as methyl, ethyl, propyl, isopropyl or amyl chloride. The salt is treated with at least about 1 mole of the alkyl chloride per mole of the salt. Normally an excess of from about 10 to 25 percent of the alkyl chloride over that needed can be used to insure complete conversion. Higher amounts can be used but are normally unnecessary.

The dialkali metal salt-organic carrier mixture can be performed sequentially by first half acidifying the salt and then reacting it will the alkyl chloride or the acidification and ester formation can be simultaneously performed.

The dialkali metal salt is reacted with the appropriate alkyl chloride at elevated temperatures. Temperatures of from about 100° C. to about 190° C. with from about 140° C. to 180° C. being preferred. The reaction is preferably performed under autogenous pressure formed from the reaction ingredients at the reaction temperatures used. These pressures are predominantly attributed to the vapor pressures of the organic carrier and the alkyl chloride used. Lower reaction pressures are obtained by using the preferred higher boiling organic carriers described above.

The present invention provides a process for forming alkyl substituted o-hydroxybenzoic acid esters without the need for separation and handling of the various intermediate products, without the need for special reactors to perform the carboxylation, and without the need to perform a high pressure carboxylation reaction.

The following examples are directed to the formation of cresotinic acid esters from cresol as an illustration of the present invention. These examples are set forth for the purposes of illustration only and are not to be construed as limitations on the present invention except as set forth in the appended claims. All parts and percentages are by weight unless otherwise indicated.

EXAMPLE I

A. Preparation of Sodium Cresolate

A five liter flask was equipped with a thermometer, dropping funnel, and stirrer. 1646 grams of a 48.6% aqueous solution of NaOH (20 moles) was added to the flask. 2163 grams of commercial o-cresol (99.4% pure, 20 moles) was added slowly over a one and one-half hour period. The temperature rose to bout 84°. Stirring was continued for an additional hour and the batch titrated as 21.1% NaOH. The sodium o-cresolate was a viscous black mass unstirrable at room temperature. It weighted 3825 grams or 191.2 grams per mole. The specific gravity at 40° C. was 1.21.

B. Dehydration 2000 ml. of xylene (1736 grams) was charged to a five liter flask equipped with a stirrer, thermometer, dropping funnel, heating mantle, Dean-Stark trap, and a reflux condenser. 630 ml. of sodium cresolate solution, (4 moles 765 grams) was charged to a dropping funnel kept at 40° – 70°. The batch was heated and a small amount of xylene distilled to insure dryness. The sodium cresolate solution was added dropwise at a pot temperature of 136°–141° C., vapor temperature of 132°–136° C. while azeotroping off water. The water volume was kept roughly in step with the addition of the sodium cresolate. At the end of five hours a total of 235 grams of water was collected. The 2261 grams of sodium cresolate xylene mixture was a readily stirrable, fine crystalline slurry.

EXAMPLE II

Preparation of Sodium Cresolate

A five liter flask was equipped with a stirrer, thermometer dropping funnel, heating mantle, Dean-Stark trap and a reflux condenser. 329 grams of a 48.6% aqueous solution of NaOH was added to the flask along with 2000 ml of a 4:1 mixture of xylene and 2-ethyl-1-hexanol. 433 grams of commercial cresol (99.4% pure) was slowly added. The batch was heated to reflux to collect the water. The product was a solution of sodium cresolate:xylene-2-ethyl-1-hexanol mixture.

EXAMPLE III

Preparation of DiSodium Salt of Cresotinic Acid

A five liter flask was equipped with a sparger, thermometer, steel stuffing box, agitator, outlet joint connected to a valve and pressure gauge. All joints were wired to prevent leaks. The 4 mole product of Example I was heated to about 106° C and $CO_2$ was bubbled in to replace the air. Heating was continued to a temperature of about 126° C. The exit valve was choked and regulated to cause a small pressure. The temperature was maintained at 128°–130° C for three hours, and at 135° C for an additional ½ hour (total 3½ hours). Pressure was maintained between 15–17 psi. The $CO_2$ valve was closed and the pressure slowly bled off through a condenser.

The volume of the batch was about 2900 ml. It had gained 110 grams of $CO_2$. Some xylene was distilled off with a NaOH trap attached which collected 16 grams of $CO_2$. The batch had absorbed 94 grams (2.1 moles) of $CO_2$.

EXAMPLE IV

Preparation of Methyl Cresotinate

A. 265 grams of solution obtained in accordance with Example III containing 0.167 mole of disodium cresotinate was introduced under $N_2$ into a round bottom flask equipped with a mechanical stirrer, gas inlet tube thermometer and drying tube. 7 grams of gaseous HCl was added. The resultant mixture was transferred into a 1 liter autoclave which was then sealed and evacuated (aspirator) at 25° C. Methyl chloride was fed into the bomb while stirring the mixture until the pressure read 23 psig (ca. 76 g methyl chloride, 1.51 moles). The bomb was then heated with stirring to 175° C (P=ca. 118 psig), and stirred for 16 hours, when T=175° C and P=ca. 113 psig. The heater was turned off and the bomb was allowed to cool at 40° C (30 psig), when it was vented slowly to the atmosphere and opened. The brown liquid and tan solid was removed (rinse with 17.2 g xylene) to give 321.2 grams of product, including rinses.

An aliquot of the product was analysed by washing 2X with 28 ml of water (pH ca. 5). The organic layer was dried with phase separation paper to give 252 grams for washed product and rinses. Derivatization and analysis by GLC gave the results shown in Table I. The water wash was acidified to pH ca. 1.5 with conc. HCl; no precipitate was obtained.

TABLE I

| Component | Product Composition % | Wt. (in 242 grams) |
| --- | --- | --- |
| Xylene | 79.4 | 192.0 |
| o-Cresol | 10.3 | 25.0 |
| MC (methyl cresotinate) | 10.5 | 25.4 |
| CA (cresotinic acid) | 0 | 0 |

The 25.4 grams of MC represents an 92% yield. The CA conversion is 100%.

B. The procedure was as Part IV-a above, but the bomb/reaction mixture was heated to 120° C (P=ca. 75 psig) initially. After stirring overnight, T=125° C (P=ca. 70 psig). The product, including 26 g of xylene rinse, weighed 304.6 grams. An aliquot was treated as above (washed weight of product and rinses equals 249 grams), and the GLC analysis are given in Table II. The aliquot water was (pH ca. 8) was acidified with concentrated HCl to pH ca. 2 to give a tan solid, mp = 161°-163° C, 100% CA by NaOH titration. The MC is equivalent to a 21% yield, assuming 22.1 grams CA (7.9%) in the original mixture.

TABLE II

| Component | Anal. Method | % of Washed Product | Wt. in 249 grams |
| --- | --- | --- | --- |
| Xylene | GLC | 87.2 | 206.0 |
| o-Cresol | GLC | 8.4 | 21.2 |
| MC | GLC | 2.1 | 5.2 |
| CA | Titration | 7.2 | 17.9 |

C. This experiment was carried out as in Part IV-A above. The HCl addition (4.0 grams) indicted 0.11 moles of CA (16.5 grams, equivalent to 18.3 grams MC), 7 grams of methyl chloride (ca. 0.14 moles) was added which resulted in a pressure of 12 psig, which fell to 0 after stirring a few minutes at 25° C. The bomb was sealed, heated to 175° C (P=76 psig) and stirred overnight, at which time the temperature was 185° C. The brown product slurry was removed (rinse as usual) to give 314.4 grams, including 34 grams of xylene rinse. An aliquot was worked up as in Example IV-A above (washed product = 332 grams) and was analyzed as is by GLC (see Table III). Acidification of the water washes (pH=5) gave no solid (CA). The 15.3 grams of MC is equivalent to 84% yield (100%=18.3 grams MC), with the CA conversion = 100%.

TABLE III

| Component | % of Washed Product | Wt. in 332 grams |
| --- | --- | --- |
| Xylene | 87.9 | 292.0 |
| o-Cresol | 7.5 | 24.9 |
| MC | 4.6 | 15.3 |

Comparison of the results of Examples IV A, B and C show that the methyl chloride reaction is predominantly temperature dependent and not pressure dependent.

EXAMPLE V

Formation of methyl o-cresotinate was done in the same manner as described above in Examples III and IV except that the sodium cresolate:xylene-2-ethyl-1-hexanol solution of Example II was used. The results were substantially the same as in Example IV above.

EXAMPLE VI

Examples IV A, B, and C were repeated except that the HCl and methyl chloride were introduced simultaneously. The results were substantially the same as above.

While the invention has been described in connection with a preferred embodiment, it is nt intended to limit the invention to the particular form set forth, but, on the contrary, it is intended to cover such alternatives, modifications and equivalents as may be included within the spirit and scope of the invention as defined by the appended claims.

What is claimed is:

1. Process for preparing an alkyl substituted o-hydroxy benzoic acid ester of the general formula:

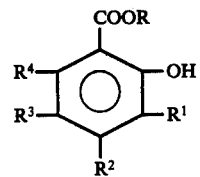

wherein R is a $C_1$-$C_5$ alkyl, $R^1$, $R^2$, $R^3$ and $R^4$ are each selected from hydrogen, or a $C_1$-$C_3$ alkyl provided that at least one of $R^1$, $R^2$, $R^3$ and $R^4$ is selected from $C_1$-$C_3$ alkyl, comprising a. reacting in an aqueous media an alkali metal hydroxide with a phenolic compound having the general formula:

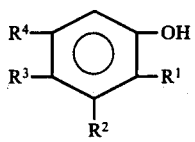

wherein $R^1$, $R^2$, $R^3$ and $R^4$ are the same as above to form an alkali metal phenolate;

b. transferring said phenolate into an organic carrier to form a substantially anhydrous phenolate-organic carrier mixture;

c. carboxylating said phenolate by contacting said mixture with sufficient $CO_2$ at substantially atmospheric pressures to form a dialkali metal salt;

d. half-neutralizing said salt by contacting the resultant salt-organic carrier mixture with about one equivalent of a substantially anhydrous inorganic acid per mole of salt; and e. reacting said salt in said organic carrier with at least about 1 mole of a $C_1$-$C_5$ alkyl chloride per mole of salt.

2. The process of claim 1 wherein steps (d) and (e) are performed simultaneously.

3. The process of claim 1 wherein $R^2$, $R^3$ and $R^4$ are hydrogen, the alkali metal hydroxide is NaOH and the alkyl chloride is methyl chloride.

4. The process of claim 1 wherein the organic carrier is selected from xylene or xylene-$C_7$-$C_{14}$ alcohol mixtures.

5. The process of claim 3 wherein the organic carrier is selected from xylene or xylene-$C_7$-$C_{14}$ alcohol mixtures.

6. The process of claim 1 wherein the reaction of alkyl chloride is carried out at from about 100°–190° C. and the carboxylation is carried out at about 100°–130° C.

7. The process of claim 3 wherein the reaction of methyl chloride is carried out at from about 100°–190° C. and the carboxylation is carried out at about 100°–150° C.

8. A process for preparing an alkyl substituted o-cresotinate comprising a. reacting an alkali metal hydroxide with cresol in an aqueous media to form an alkali metal cresoylate;

b. transferring said cresylate to an organic carrier to form a substantially anhydrous cresylate-organic carrier mixture;

c. carboxylating said cresylate by contacting said mixture with sufficient $CO_2$ to form a dialkali metal salt;

d. acidifying said salt with about 1 equivalent of a substantially anhydrous inorganic acid per mole of salt; and e. reacting at elevated temperatures said salt with at least one mole of a $C_1$-$C_5$ alkyl chloride.

9. The process of claim 8 wherein the alkali metal is sodium and the elevated temperature of steps (b) and (d) is from about 100° C to 190° C.

10. The process of claim 9 wherein the organic carrier is selected from xylene or xylene-$C_7$-$C_{14}$ alcohol mixture.

11. The process of claim 8 wherein steps (d) and (e) are done simultaneously.

12. The process of claim 8 wherein the alkali metal hydroxide is NaOH and the alkyl chloride is methyl chloride.

13. The process of claim 3 wherein the inorganic acid is HCl.

14. The process of claim 12 wherein the inorganic acid is HCl.

15. A process for preparing an alkyl substituted o-hydroxybenzoic acid ester of the general formula:

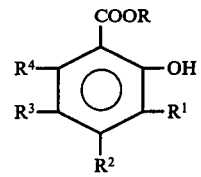

wherein R is a $C_1$-$C_5$ alkyl, and $R^1$, $R^2$, $R^3$ and $R^4$ are each selected from hydrogen or a $C_1$-$C_3$ alkyl provided that at least one $R^1$, $R^2$, $R^3$ or $R^4$ is a $C_1$-$C_3$ alkyl comprising acidifying in an organic carrier a dialkali metal salt of the general formula:

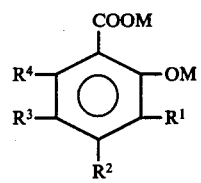

wherein M is an alkali metal and $R^1$, $R^2$, $R^3$ and $R^4$ are the same as above with about 1 mole of HCl per mole of salt and reacting said salt in said organic carrier with 1 mole of $C_1$-$C_5$ alkyl chloride per mole of salt.

16. The process of claim 15 wherein the acidifying with HCl and reacting with alkyl chloride is done simultaneously.

17. Process for preparing an alkyl substituted o-hydroxy benzoic acid ester of the general formula:

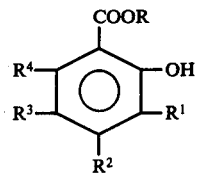

wherein R is a $C_1$-$C_5$ alkyl, $R^1$, $R^2$, $R^3$ and $R^4$ are each selected from hydrogen, or a $C_1$-$C_3$ alkyl provided that at least one of $R^1$, $R^2$, $R^3$ or $R^4$ is selected from $C_1$-$C_3$ alkyl, comprising a. introducing an aqueous solution or an alkali metal hydroxide into an organic carrier containing a phenolid compound of the formula:

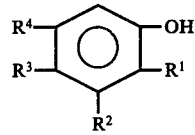

wherein $R^1$, $R^2$, $R^3$ and $R^4$ are the same as above to form an alkali metal phenolate;

b. removing the water present in the organic carrier to form a substantially anhydrous phenolate-organic carrier mixture;

c. contacting said mixture at substantially atmospheric pressure with sufficient $CO_2$ to form a dialkali metal salt;
d. half-neutralizing said salt in said organic carrier with about one equivalent of a substantially anhydrous inorganic acid per mole of salt; and
e. reacting said salt in said organic carrier with at least about one mole of a $C_1$-$C_5$ alkyl chloride per mole of salt.

18. The process of claim 17 wherein $R^1$ is methyl, $R^2$, $R^3$ and $R^4$ are each hydrogen.

19. The process of claim 18 wherein steps (d) and (e) are done simultaneously.

20. The process of claim 17 wherein $R^1$ is methyl, $R^2$, $R^3$ and $R^4$ are each hydrogen; step (c) is performed at about 100° to 150° C; step (e) is carried out at from about 100° to 190° C; and the $C_1$-$C_5$ alkyl chloride is methyl chloride.

21. The process of claim 20 wherein the alkali metal hydroxide is NaOH; the acid is HCl, and steps (d) and (e) are carried out simultaneously.

* * * * *